United States Patent
Nirogi et al.

(10) Patent No.: US 9,540,321 B2
(45) Date of Patent: Jan. 10, 2017

(54) PROCESS FOR LARGE SCALE PRODUCTION OF 1-[(2-BROMOPHENYL)SULFONYL]-5-METHOXY-3-[(4-METHYL-1-PIPERAZINYL)METHYL]-1H-INDOLE DIMESYLATE MONOHYDRATE

(71) Applicant: SUVEN LIFE SCIENCES LIMITED, Hyderabad, Andhra Pradesh (IN)

(72) Inventors: Ramakrishna Nirogi, Hyderabad (IN); Rama Sastri Kambhampati, Hyderabad (IN); Anil Karbhari Shinde, Hyderabad (IN); Venkateswarlu Jasti, Hyderabad (IN)

(73) Assignee: SUVEN LIFE SCIENCES LIMITED, Hyderbad (IN)

( * ) Notice: Subject to any disclaimer, the term of this patent is extended or adjusted under 35 U.S.C. 154(b) by 0 days.

(21) Appl. No.: 15/100,489

(22) PCT Filed: Feb. 20, 2014

(86) PCT No.: PCT/IN2014/000109
§ 371 (c)(1),
(2) Date: May 31, 2016

(87) PCT Pub. No.: WO2015/083179
PCT Pub. Date: Jun. 11, 2015

(65) Prior Publication Data
US 2016/0297759 A1   Oct. 13, 2016

(30) Foreign Application Priority Data
Dec. 2, 2013 (IN) .......................... 5537/CHE/2013

(51) Int. Cl.
C07D 209/14 (2006.01)

(52) U.S. Cl.
CPC .................................. *C07D 209/14* (2013.01)

(58) Field of Classification Search
None
See application file for complete search history.

(56) References Cited

FOREIGN PATENT DOCUMENTS

| WO | 2004/048330 | 6/2004 |
| WO | 2004/055026 | 7/2004 |

OTHER PUBLICATIONS

European Patent Office, "International Search Report", mailed Aug. 25, 2014 in PCT Application No. PCT/IN2014/000109, filed Feb. 20, 2014.
European Patent Office, "Written Opinion", mailed Aug. 25, 2014 in PCT Application No. PCT/IN2014/000109, filed Feb. 20, 2014.

*Primary Examiner* — Emily Bernhardt
(74) *Attorney, Agent, or Firm* — IPHorgan LTD.

(57) ABSTRACT

A process suitable for adoption to large scale manufacture of 1-[(2-bromophenyl-sulfonyl]-5-methoxy-3-[(4-methyl-1-piperazinyl)methyl]-1H-indole dimesylate monohydrate, which is a selective 5-HT$_6$ receptor antagonist intended for the symptomatic treatment of Alzheimer's disease and other disorders of memory and cognition like Attention deficit hyperactivity, Parkinson's and Schizophrenia.

12 Claims, No Drawings

PROCESS FOR LARGE SCALE PRODUCTION OF 1-[(2-BROMOPHENYL)SULFONYL]-5-METHOXY-3-[(4-METHYL-1-PIPERAZINYL)METHYL]-1H-INDOLE DIMESYLATE MONOHYDRATE

CROSS REFERENCE TO RELATED APPLICATIONS

This application is a national stage completion application of PCT Application No. PCT/IN2014/000109, filed Feb. 20, 2014, and claims the benefit of India Application No. 5537/CHE/2013, filed Dec. 2, 2013. Each of these applications is incorporated by reference herein in its entirety.

FIELD OF INVENTION

The present invention comprises of process for the synthesis of 1-[(2-bromophenyl)sulfonyl]-5-methoxy-3-[(4-methyl-1-piperazinyl)methyl]-1H-indole dimesylate monohydrate, which is suitable for adaptation to large scale manufacturing.

BACKGROUND OF THE INVENTION $5\text{-HT}_6$ receptor is one of the potential therapeutic target for the development of cognitive enhancers. $5\text{-HT}_6$ receptor is localized exclusively in central nervous system, in areas important for learning and memory. In recent years several studies have shown that $5\text{-HT}_6$ receptor antagonists show beneficial effect on cognition in several animal models. Several $5\text{-HT}_6$ antagonists advanced into clinic.

1-[(2-Bromophenyl)sulfonyl]-5-methoxy-3-[(4-methyl-1-piperazinyl)methyl]-1H-indole. Dimesylate monohydrate is a promising pharmaceutical agent, which is a selective $5\text{-HT}_6$ receptor antagonist intended for the symptomatic treatment of Alzheimer's disease and other disorders of memory and cognition like Attention deficit hyperactivity, Parkinson's and Schizophrenia.

Currently 1-[(2-bromophenyl)sulfonyl]-5-methoxy-3-[(4-methyl-1-piperazin-1-yl)methyl]-1H-indole dimesylate monohydrate is undergoing clinical trials designed to confirm its efficacy. The demand for 1-[(2-bromophenyl)sulfonyl]-5-methoxy-3-[(4-methyl-1-piperazinyl)methyl]-1H-indole dimesylate monohydrate as a drug substance has increased substantially with the advent of its clinical testing. The future need for much larger amounts is projected due to the intended commercialization of 1-[(2-bromophenyl)sulfonyl]-5-methoxy-3-[(4-methyl-1-piperazinyl)methyl]-1H-indole dimesylate mono hydrate.

For the person skilled in art, it is a well known fact that various parameters will change during the manufacture of a compound on a large scale when compared to the synthetic procedures followed in laboratory. Therefore, there is need to establish and optimize large scale manufacturing process. 1-[(2-bromophenyl)sulfonyl]-5-methoxy-3-[(4-methyl-1-piperazinyl)methyl]-1H-indole and it's pharmaceutically acceptable salts and their syntheses were disclosed by Ramakrishna et al. in WO 2004/048330. The process for the preparation of 1-[(2-bromophenyl)sulfonyl]-5-methoxy-3-[(4-methyl-1-piperazinyl)methyl]-1H-indole dimesylate monohydrate disclosed herein was proved to be unsatisfactory for adaptation to the large scale manufacturing. Hence it became highly desirable to establish the manufacturing process of 1-[(2-bromophenyl)sulfonyl]-5-methoxy-3-[(4-methyl-1-piperazinyl)methyl]-1H-indole dimesylate monohydrate. Therefore, we established and optimized the manufacturing process of 1-[(2-bromophenyl)sulfonyl]-5-methoxy-3-[(4-methyl-1-piperazinyl)methyl]-1H-indole dimesylate, monohydrate, which is amenable to large scale synthesis of 1-[(2-bromophenyl)sulfonyl]-5-methoxy-3-[(4-methyl-1-piperazinyl)methyl]-1H-indole dimesylate monohydrate.

SUMMARY OF THE INVENTION

The main object of the present invention is to provide a large scale, well optimized manufacturing process for 1-[(2-bromophenyl)sulfonyl]-5-methoxy-3-[(4-methyl-1-piperazinyl)methyl]-1H-indole dimesylate monohydrate.

Another object of the invention is to provide a process to obtain substantially pure 1-[(2-bromophenyl)sulfonyl]-5-methoxy-3-[(4-methyl-1-piperazinyl)methyl]-1H-indole dimesylate mono hydrate.

Another object of this invention is to show the compatibility of the process to produce 1-[(2-bromophenyl)sulfonyl]-5-methoxy-3-[(4-methyl-1-piperazinyl)methyl]-1H-indole dimesylate mono hydrate on a large scale using standard larger scale chemical process equipment.

Yet another object of this invention is to provide a commercial process for the production of 1-[(2-bromophenyl)sulfonyl]-5-methoxy-3-[(4-methyl-1-piperazinyl)methyl]-1H-indole dimesylate monohydrate on a larger scale.

DETAILED DESCRIPTION OF THE INVENTION

The large scale manufacturing process for preparation of 1-[(2-bromophenyl)sulfonyl]-5-methoxy-3-[(4-methyl-1-piperazinyl)methyl]-1H-indole dimesylate monohydrate of formula (I) of the present invention is illustrated by the Scheme-1 as given below:

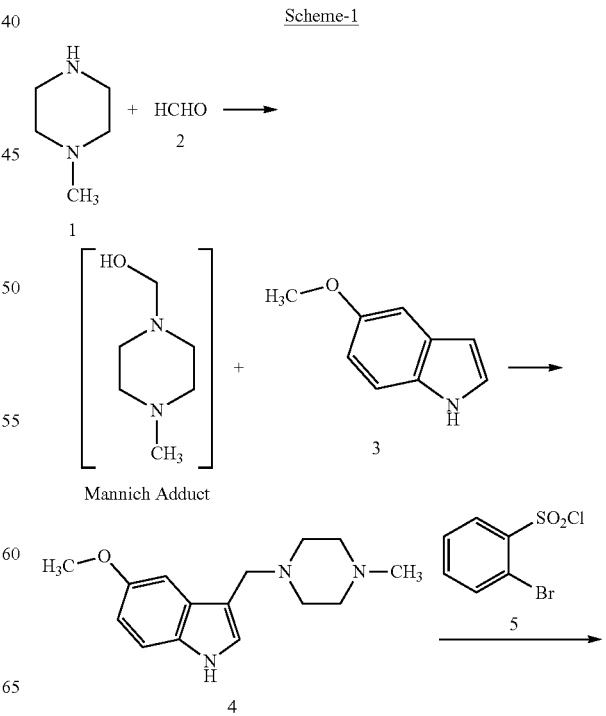

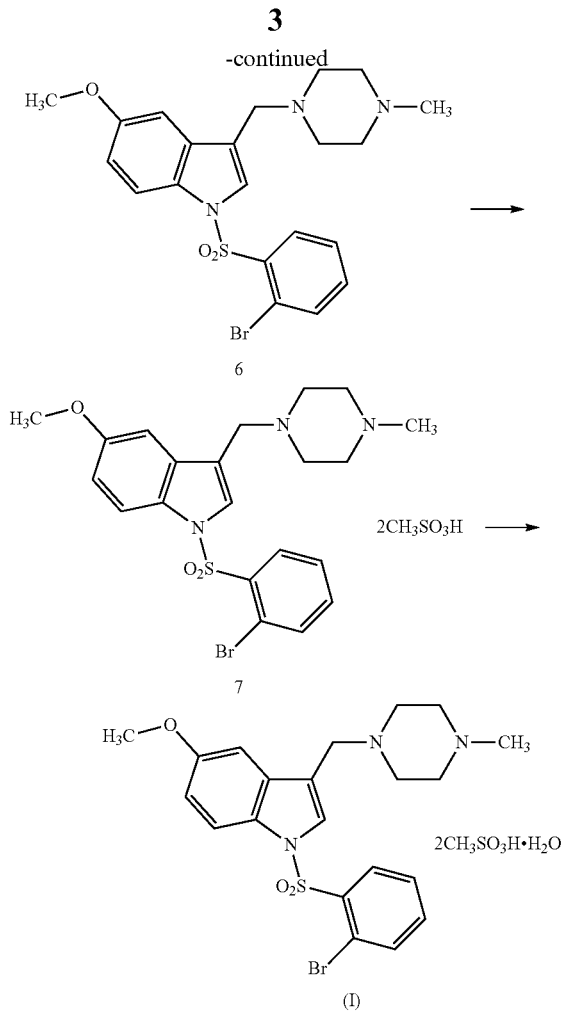

Step (i):

Converting 1-Methylpiperazine of formula 1 in presence of acetic acid and aqueous formaldehyde of formula 2 to obtain Mannich adduct. The reaction temperature may range from 15° C. to 35° C. and preferably at a temperature in the range from 20° C. to 30° C. The duration of the reaction may range from 1.5 hours to 2.5 hours, preferably for a period of 2 hours.

Step (ii):

Reacting the Mannich adduct, as obtained above, with 5-methoxyindole of formula 3 in presence of methanol to obtain technical Mannich base, 5-methoxy-3-[(4-methyl-1-piperazinyl)methyl]-1H-indole of formula 4. The reaction temperature may range from 15° C. to 40° C. and preferably at a temperature in the range from 20° C. to 35° C. The duration of the reaction may range from 2.5 hours to 3.5 hours, preferably for a period of 3 hours.

Step (iii):

The above obtained technical Mannich base, 5-methoxy-3-[(4-methyl-1-piperazinyl)methyl]-1H-indole of formula 4 was crystallized in toluene by heating the solution to 85-95° C. for a period of 1 hour, followed by cooling the solution to 10° C.-15° C. for a period of 3 hours.

Step (iv):

The above obtained crystallized 5-methoxy-3-[(4-methyl-1-piperazinyl)methyl]-1H-indole of formula 4 is recrystallized in toluene by heating the solution to 95-105° C. for a period of 2 hour, followed by cooling the solution to 10° C.-15° C. for the period of 3 hours.

Step (v):

Reacting the above obtained crystalline 5-methoxy-3-[(4-methyl-1-piperazinyl)methyl]-1H-indole of formula 4 with 2-bromobenzenesulfonyl chloride of formula 5 in tetrahydrofuran in presence of potassium hydroxide to obtain 1-[(2-bromophenyl)sulfonyl]-5-methoxy-3-[(4-methyl-1-piperazinyl)methyl]-1H-indole of formula 6. The reaction temperature may range from 20° C. to 40° C. and preferably at a temperature ranging from 25° C. to 35° C. The duration of the reaction may range from 3.5 hours to 4.5 hours, preferably for a period of 4 hours.

Step (vi):

Converting the above obtained 1-[(2-bromophenyl)sulfonyl]-5-methoxy-3-[(4-methyl-1-piperazinyl)methyl]-1H-indole of formula 6 in presence of ethanol and methanesulfonic acid to 1-[(2-bromophenyl)sulfonyl]-5-methoxy-3-[(4-methyl-1-piperazinyl)methyl]-1H-indole dimesylate of formula 7. The reaction temperature may range from 15° C. to 35° C. and preferably at a temperature ranging from 25° C. to 30° C. The duration of the reaction may range from 18 hours to 24 hours, preferably for a period of 24 hours.

Step (vii):

Converting the above obtained 1-[(2-bromophenyl)sulfonyl]-5-methoxy-3-[(4-methyl-1-piperazinyl)methyl]-1H-indole dimesylate of formula 7 in presence of aqueous ethanol and carbon slurry to obtain 1-[(2-bromophenyl)sulfonyl]-5-methoxy-3-[(4-methyl-1-piperazinyl)methyl]-1H-indole dimesylate monohydrate of formula (I). The reaction temperature may range from 75° C. to 85° C. and preferably at a temperature in the range from 75° C. to 80° C. The duration of the reaction may range from 0.5 hour to 1.5 hours, preferably for a period of 45 minutes.

The details of the invention are given in example provided below. The entire process operations were carried out under nitrogen blanket:

Example 1

Preparation of 1-[(2-bromophenyl)sulfonyl]-5-methoxy-3-[(4-methyl-1-piperazinyl)methyl]-1H-indole dimesylate monohydrate Step (i) & (ii): Preparation of 5-methoxy-3-[(4-methyl-1-piperazinyl)methyl]-1H-indole Step (i):

1-Methylpiperazine (15 Kg, 0.15 Kg Mole) was charged into a reactor. The mass was cooled to 5-10° C. Demineralised water (12 Kg) was added to the above mass slowly, maintaining the mass temperature 10° C.-20° C., over a period of 30 minutes. Then added acetic acid (6.16 Kg, 0.103 Kg Mole) to the above mass in 30 minutes, maintaining the mass temperature at 10° C.-20° C. The mass was further stirred for another 15-20 minutes at 10° C.-20° C. and aqueous formaldehyde solution (15.67 Kg, 30% w/v, 0.1567 Kg Mole) was added in 60 minutes maintaining the mass temperature at 15-20° C. The resultant thick, red colored reaction mass was stirred for another 2 hours at 20° C.-30° C. to obtain the mannich adduct.

Step (ii):

Simultaneously in a separate reactor 125 Kg of methanol was charged at 25-35° C. 5-methoxyindole (20 Kg, 0.1359 Kg Mole) was added and the mass was stirred to obtain a clear solution. The mass was cooled to 8° C.-10° C. in 1.5 hours by circulating brine in the reactor jacket. The Mannich adduct, prepared as above, was charged into the reactor containing cooled methanolic solution of 5-methoxyindole from an addition tank over a period of 50-60 minutes, while maintaining the temperature of the reaction mass at 8° C.-16° C. After completion of addition, the mass temperature was allowed to rise to 20° C.-35° C. Then the reaction mass was further stirred for 3 hours at 20° C.-35° C. After completion of the reaction (thin layer chromatography), the reaction mass was discharged into clean and dry containers.

Another reactor was charged with 400 L of demineralised water followed by the addition of 20 Kg of lye solution at 20° C.-35° C. The content was cooled to 10° C.-15° C. under stirring. The above reaction mass in the containers was added to the reactor, maintaining the mass temperature at 10° C.-15° C. in 30-40 minutes. The final pH of the solution was adjusted to 9-12, if necessary by adding some more lye solution. Then the product was extracted with ethyl acetate (1×260 L & 4×160 L) maintaining the mass temperature at 10° C.-15° C. during the entire operations. The pH of aqueous layer was adjusted to 9-12 before each extraction.

The combined organic layer was washed with (2×170 Kg) of brine solution (the brine solution was prepared by adding 95 Kg of vacuum salt to 245 Kg of demineralised water) at 20° C.-35° C. The total organic extracts, obtained after the brine washing, were dried over 35 Kg of anhydrous sodium sulfate under stirring for 30 minutes at 20° C.-35° C.

The organic layer was filtered and charged into another clean reactor. The solvent was removed totally under 500-600 mm of Hg vacuum, at 20° C.-45° C.

The residual mass, thus obtained, was cooled to room temperature and charged 60 L toluene and stirred the contents at 20° C.-45° C. for 15 minutes. The solvent was distilled off under reduced pressure (500-700 mm of Hg vacuum) at 45-65° C. The operation was repeated again by the addition of 60 L toluene and stirring the contents at 20° C.-45° C. for 15 min. The solvent was distilled off under reduced pressure (500-700 mm of Hg vacuum) at 45-65° C. again to ensure total removal of ethylacetate to avoid losses during recrystallization step. The residual technical product, 5-methoxy-3-[(4-methyl-1-piperazinyl)methyl]-1H-indole, thus obtained, was recrystallized twice, as per the details given below, to obtain the product of desired purity.

Step (iii): Crystallization of 5-methoxy-3-[(4-methyl-1-piperazinyl)methyl]-1H-indole Charged 61 Kg of toluene into the above reactor which contains the technical product, 5-methoxy-3-[(4-methyl-1-piperazinyl)methyl]-1H-indole. The contents were heated to 85-95° C. and maintained for an hour at 85-95° C. The clear solution, thus obtained, was allowed to cool to 30° C.-40° C. by circulating room temperature water in the reactor jacket. The mass was further cooled to 10° C.-15° C. and maintained for 3 hours at the same temperature. The crystalline solid mass was filtered through nutsche and the solid on the nutsche was washed with 18 L of chilled (10° C.-15° C.) toluene and sucked well. The material was further washed with 20 L of n-hexane and sucked dry to obtain 22.7 Kg of crystalline material.

Step (iv): Recrystallization of 5-methoxy-3-[(4-methyl-1-piperazinyl)methyl]-1H-indole Charged 40 Kg of toluene into a reactor followed by the addition of the 5-methoxy-3-[(4-methyl-1-piperazinyl)methyl]-1H-indole (22.7 Kg) obtained in the first crystallization step under stirring. The contents were heated to 95-105° C. and maintained for 2 hours to obtain a clear solution. The mass was allowed to cool to 35° C.-40° C. by circulating room temperature water in the jacket. It was further cooled to 10° C.-15° C. and maintained for 3 hours at 10° C.-15° C. The crystalline solid mass was filtered through nutsche and the solid on the nutsche was washed with 8 L of chilled (10° C.-15° C.) toluene and sucked well. The material was further washed with 15 L of n-hexane and sucked dry. The material was further dried in tray driers at 20° C.-25° C. to obtain the title product, as off white crystalline powder.

Weight of the crystallized material: 19.95 Kg;
Yield (based on 5-methoxyindole charged): 56.6%;
HPLC purity: 99.74%;
Total impurities: 0.26%;
Assay: 100.6%;
Moisture content: 0.24%;
Melting range (° C.): 139-140.6;
IR spectra (cm$^{-1}$): 3125, 2951, 1875, 1622, 1585, 1492, 1351, 1288, 1215, 1059, 930, 654;
$^1$H-NMR (CDCl$_3$, δ ppm): 2.30 (3H, s), 2.5 (8H, bs), 3.71 (2H, s), 3.86 (3H, s), 6.83-6.86 (1H, dd, J=8.81, 2.7 Hz), 7.01 (1H, d, J=2.06 Hz), 7.18-7.20 (2H, m), 8.91 (1H, s);
$^{13}$C-NMR (CDCl$_3$, δ ppm): 45.89, 52.79, 53.39, 55.11, 55.83, 101.3, 111.39, 111.75, 111.81, 124.88, 128.45, 131.48, 153.77;
Mass [M+H]$^+$: 260.3.

Step (v): Preparation of 1-[(2-bromophenyl)sulfonyl]-5-methoxy-3-[(4-methyl-1-piperazinyl)methyl]-1H-indole Tetrahydrofuran (85.78 Kg) was charged into a reactor at 20° C.-35° C. Then charged the crystallized 5-methoxy-3-[(4-methyl-1-piperazinyl)methyl]-1H-indole (21.5 Kg, 0.0829 Kg Mole) into the reactor at 20-35° C. and stirred the mass well. The mass was cooled to 10° C.-20° C. with chilled water in the jacket. Charged powdered potassium hydroxide (16.11 Kg) to the above suspension at 10° C.-20° C. in 10 minutes under stirring. Slight exotherm was observed. Mass temperature rose from 15.1° C. to 16.3° C. The mass was further stirred for 60 minutes at 10° C.-20° C. A solution of 2-bromobenzenesulfonyl chloride (27.71 Kg, 0.1084 Kg Mole) in 41.72 Kg tetrahydrofuran was added through addition tank at a constant rate in 60 minutes at 10° C.-30° C. The reaction was exothermic and the mass temperature went up from 16° C. to 30° C. Then removed the chilled water from the jacket and stirred the mass for 3 hours at 25° C.-35° C. As the reaction was progressing the mass thickened due to formation of potassium chloride. The progress of the reaction was monitored by thin layer chromatography (Eluent system: Chloroform and Methanol in 8:2 ratio and the product is relatively non-polar). Since thin layer chromatography shows the presence of starting material (5-methoxy-3-[(4-methyl-1-piperazinyl)methyl]-1H-indole), another lot of 2-bromo benzenesulfonyl chloride (4.5 Kg, 0.0176 Kg Mole) dissolved in 13.71 Kg tetrahydrofuran was added to the reaction mass at 30° C. in 25 minutes. No exotherm observed. The reaction mass was further stirred for 60 minutes at 30° C.-35° C. Since the starting material was absent as per thin layer chromatography, it was taken for further workup.

In the mean while charged 360 L demineralised water into another reactor and cooled the contents to 10° C.-15° C. The above reaction mass was quenched into chilled water in 60 minutes (mass temperature was 12.1° C.). The pH of the reaction mass was adjusted to ~9.5 with an aqueous solution of potassium hydroxide. The product was extracted with (4×155 L) ethyl acetate maintaining the mass temperature at 10° C.-15° C. The pH of aqueous layer was adjusted to ~9.5 before each extraction. The combined organic layer was taken for extraction of the product into aqueous acetic acid.

Acetic acid (8.69 Kg, 0.1448 Kg mole) was dissolved in 137 L of demineralised water and cooled the mass to 10° C.-15° C. Charged the above organic extracts into it and stirred for 30 minutes at 10° C.-15° C. The mass was allowed to settle for 20 minutes and separated the bottom aqueous acetic acid extract containing the product into a fresh clean reactor.

Further, the extraction and separation process with fresh aqueous acetic acid solution was repeated thrice using 3×145 Kg of aqueous acetic acid solution (prepared by dissolving 25.74 Kg, 0.429 Kg Mole of acetic acid in 412 L of demineralised water) following the similar procedure mentioned above, maintaining mass temperature at 10° C.-15° C. The combined aqueous acetic acid extracts (containing the product) were taken into the reactor. It was washed with 44 L of ethyl acetate by stirring the mass at 10° C.-15° C. for 15 minutes, followed by 15 minutes settling. The aqueous product layer was separated. The pH of the aqueous solution was found to be 4.5. The mass was cooled to 10° C.-15° C. and the pH of the solution was adjusted to ~9.5 with chilled caustic lye solution (31 Kg). The product was extracted with (4×155 L) of ethyl acetate, maintaining the mass temperature at 10° C.-15° C. The pH of aqueous layer was adjusted to ~9.5 before each extraction.

The organic layer was washed with (2×112 Kg) brine solution (prepared from 51.6 Kg vacuum salt and 175 L water) at 10° C.-15° C. The organic layer was dried over 32 Kg of anhydrous sodium sulfate at 20° C.-35° C. and filtered into another clean reactor. Solvent was removed under 500-600 mm Hg by circulating 50-55° C. water in the jacket of the reactor.

To the residual mass in the reactor after solvent removal, charged 36 L of methanol followed by 72 L of isopropanol. The reaction mass was heated to reflux temperature (65° C.-75° C.). At mass temperature ~70° C. a clear solution was obtained. The mass was allowed to cool to 35-45° C. with room temperature water circulation in the reactor jacket. Further, it was cooled to 15-20° C. by circulating brine in the jacket and maintained under stirring for 2 hours at 15° C.-20° C. The solids were filtered through nutsche and sucked well under vacuum. The cake was washed with 36 L of isopropanol (15-20° C.) and sucked well. The wet solid material (37.76 Kg) was taken in tray drier and air dried at 25° C.-35° C. for 60 minutes. Further, it was dried at 40° C.-45° C. for 6 hours to obtain 32.64 Kg of the title product.

Overall Yield: 82.3% (based on Mannich base charged);
HPLC purity: 99.36%;
Single major impurity: 0.29%;
Total impurities: 0.64%;
Assay: 100.5%;
Loss on drying at 105° C.: 0.21%;
Melting range (° C.): 128.1-129.2;
IR spectra (cm$^{-1}$): 2931, 2786, 1607, 1474, 1369, 1222, 1178, 1032, 737, 597;
$^1$H-NMR (CDCl$_3$, δ ppm): 2.29 (3H, s), 2.32-2.50 (8H, bs), 3.62 (2H, s), 3.83 (3H, s), 6.83-6.86 (1H, dd, J=8.98, 2.46 Hz), 7.19-7.20 (1H, d, J=2.42 Hz), 7.36-7.40 (1H, dt, J=7.68, 1.56 Hz), 7.45-7.47 (1H, t, J=7.50 Hz), 7.53-7.55 (1H, d, J=9.00, Hz), 7.64-7.66 (2H, m), 8.03-8.05 (1H, dd, J=7.89, 1.54 Hz);

$^{13}$C-NMR (CDCl$_3$, δ ppm): 45.94, 53.07, 53.33, 55.17, 55.60, 103.28, 113.20, 113.69, 117.83, 120.42, 127.05, 127.69, 129.57, 131.16, 131.57, 134.48, 135.90, 138.09, 156.12;
Mass [M+H]$^+$: 478.1, 480.1.

Step (vi): Preparation of 1-[(2-bromophenyl)sulfonyl]-5-methoxy-3-[(4-methyl-1-piperazinyl)methyl]-1H-indole dimesylate Charged 182.5 Kg of absolute ethanol into a reactor at 20° C.-35° C. Then charged 1-[(2-bromophenyl)sulfonyl]-5-methoxy-3-[(4-methyl-1-piperazinyl)methyl]-1H-indole (obtained in the above step, 32.02 Kg, 0.067 Kg Mole) under stirring in a single lot at 20° C.-35° C. (mass temperature), added methanesulfonic acid (13.9 Kg, 0.1446 Kg Mole) slowly to the above reaction mass from a holding tank in 60 minutes, maintaining mass temperature at 20° C.-35° C. No clear solution was obtained at any stage. The mass became thick, but stirrable. The reaction mass was stirred for 24 hours maintaining mass temperature between 25° C.-30° C. The mass was filtered through nutsche under nitrogen atmosphere and it was sucked well. The cake, thus obtained, was washed thoroughly with 48 L of ethyl alcohol (slurry wash), sucked well and the cake was again washed with 18 L of ethyl alcohol (spray wash) followed by washing with n-hexane (27 L). It was sucked dry to obtain 70.23 Kg wet cake. The wet cake was taken in a tray drier and dried at 20° C.-35° C. for 10 hours to obtain 49.43 Kg product (LOD: ~9.57%).

Weight of product on dry basis: 44.65 Kg
Yield of salt: Quantitative (based on 1-[(2-bromophenyl)sulfonyl]-5-methoxy-3-[(4-methyl-1-piperazinyl)methyl]-1H-indole charged);
HPLC purity: 99.69%;
Total impurities: 0.31%;
Salt content: 27.39%.

Step (vii): Preparation of 1-[(2-bromophenyl)sulfonyl]-5-methoxy-3-[(4-methyl-1-piperazinyl)methyl]-1H-indole dimesylate monohydrate Charged 415 Kg of aqueous ethanol (95% ethanol & 5% water) into a reactor, followed by the addition of 1-[(2-bromophenyl)sulfonyl]-5-methoxy-3-[(4-methyl-1-piperazinyl)methyl]-1H-indole dimesylate (44.65 Kg, 0.0666 Kg Mole, obtained from the above step) at 20° C.-35° C. In the meanwhile carbon slurry was prepared separately by adding 6.7 Kg of carbon powder into 18 Kg of aqueous ethanol (95% ethanol & 5% water). Then the carbon slurry was transferred to the reactor and the reaction mass was heated at 75-80° C. by circulating 80° C.-90° C. hot water in the reactor jacket for 45 minutes. The mass was filtered hot into another clean reactor, washed the carbon bed with 54.25 Kg of aqueous ethanol (95% ethanol & 5% water) at 75-80° C. The contents of the reactor were heated at reflux temperature (76° C.-78° C.) for 30 minutes to obtain a clear solution. The mass was allowed to cool on its own to 45° C. in 10 hours by applying compressed air in the reactor jacket. It was further cooled to 10° C.-15° C. with chilled water circulated in the jacket and maintained under stirring for 3 hours. Filtered the crystalline material through a centrifuge and the material on the centrifuge was washed with 18.6 Kg of aqueous ethanol (95% ethanol & 5% water) (10° C.-15° C.) and spin dried. The whole material was air dried in a tray drier for 14 hours at 20° C.-35° C. The material was milled, sieved and collected in poly bag to obtain 37.7 Kg of the title product. The uniform material was sampled for analysis.

Weight of dry product: 37.7 Kg;
Yield of salt: 82.2%;
HPLC purity: 99.7%;
Single impurity: 0.3%;
Assay: 99.9%;
Moisture content: 2.61%;
Salt content (Dimesylate): 27.56%;
Melting range (° C.): 218.0-220.0;
IR spectra (cm$^{-1}$): 3148, 3012, 1611, 1590, 1471, 1446, 1439, 1382, 1220, 1194, 1180, 1045, 775, 596;
$^1$H-NMR (D2O, δ ppm): 2.65 (6H, s), 2.89 (3H, s), 3.52 (8H, bs), 3.70 (3H, s), 4.46 (2H, s), 6.75-6.78 (1H, dd, J=9.07, 2.02 Hz), 7.10-7.11 (1H, d, J=1.9 Hz), 7.32-7.38 (2H, m), 7.44-7.47 (1H, t, J=7.6 Hz), 7.54-7.56 (1H, dd, J=7.79 Hz), 8.04 (1H, s), 8.14-8.16 (1H, d, J=7.94 Hz);
$^{13}$C-NMR (δ ppm): 38.42, 42.79, 48.19, 50.35, 55.80, 102.57, 108.20, 113.72, 114.07, 119.62, 128.25, 128.56, 130.17, 131.80, 132.15, 135.28, 135.95, 156.21;
Mass [M+H]$^+$: 478, 480.

Advantages

1. In this patent application, robust and well optimized process for the manufacture of 1-[(2-bromophenyl)sulfonyl]-5-methoxy-3-[(4-methyl-1-piperazinyl)methyl]-1H-indole dimesylate mono hydrate is disclosed. This process is suitable for large scale manufacturing of 1-[(2-bromophenyl)sulfonyl]-5-methoxy-3-[(4-methyl-1-piperazinyl) methyl]-1H-indole dimesylate mono hydrate without any trial and error.
2. Pharmaceutically acceptable dimesylate salt of the 1-[(2-bromophenyl)sulfonyl]-5-methoxy-3-[(4-methyl-1-piperazinyl)methyl]-1H-indole base was manufactured utilizing commercially available and economically viable raw materials.
3. The process offers purification of 1-[(2-bromophenyl) sulfonyl]-5-methoxy-3-[(4-methyl-1-piperazinyl)methyl]-1H-indole base by aqueous acetic acid treatment followed by recrystallization from methanol and isopropanol mixture to get rid of closely related undesirable impurities.
4. The process described in this patent application does not involve column purifications at any stage. Crystallization methods were developed at each stage to obtain pure product, thereby eliminating the material handling issues.
5. The process involves crystalline products at all the isolated intermediate stages. Therefore, the disclosed process is suitable for further scaling up to ton's level.

We claim:
1. A process suitable for large scale production of 1-[(2-bromophenyl)sulfonyl]-5-methoxy-3-[(4-methyl-1-piperazinyl)methyl]-1H-indole dimesylate monohydrate of formula (I),

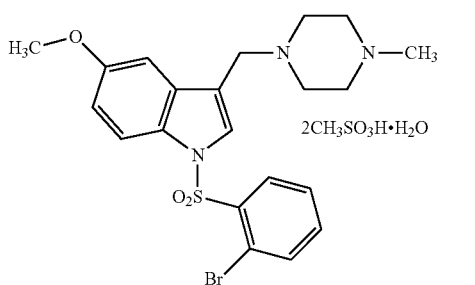

(I) 2CH$_3$SO$_3$H•H$_2$O which comprises:
Step (i): reacting 1-methylpiperazine of formula 1

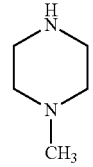

1 in presence of acetic acid and aqueous formaldehyde of formula 2

HCHO      2 at a temperature in the range of 15° C. to 35° C. for a period of 1.5 hours to 2.5 hours to obtain Mannich adduct;

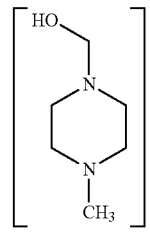

Mannich Adduct

Step (ii): reacting the Mannich adduct with 5-methoxyindole of formula 3

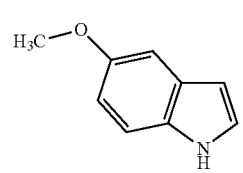

3 in presence of methanol at a temperature in the range of 15° C. to 40° C. for a period of 2.5 hours to 3.5 hours to obtain 5-methoxy-3-[(4-methyl-1-piperazinyl) methyl]-1H-indole of formula 4;

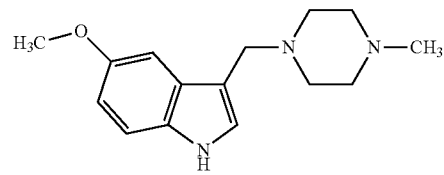

4

Step (iii): crystallizing 5-methoxy-3-[(4-methyl-1-piperazinyl) methyl]-1H-indole of formula 4 in toluene by heating the solution to 85° C.-95° C. for a period of 1 hour, followed by cooling the solution to 10° C.-15° C. for the period of 3 hours;
Step (iv): recrystallizing 5-methoxy-3-[(4-methyl-1-piperazinyl) methyl]-1H-indole of formula 4 in toluene by heating the solution to 95° C.-105° C. for a period of 2 hours, followed by cooling the solution to 10° C. 15° C. for a period of 3 hours;

Step (v): reacting the above obtained crystalline 5-methoxy-3-[(4-methyl-1-piperazinyl) methyl]-1H-indole of formula 4 with 2-bromobenzenesulfonyl chloride of formula 5;

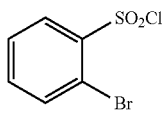
5 in presence of tetrahydrofuran and potassium hydroxide at a temperature in the range of 20° C. to 40° C. for a period of 3.5 hours to 4.5 hours to obtain 1-[(2-bromophenyl)sulfonyl]-5-methoxy-3-[(4-methyl-1-piperazinyl)methyl]-1H-indole of formula 6;

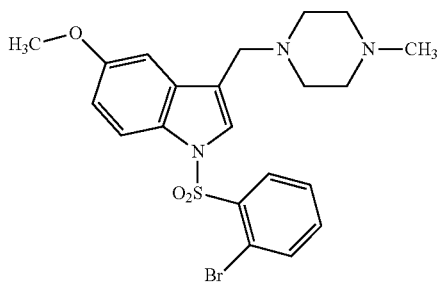
6

Step (vi): converting 1-[(2-bromophenyl)sulfonyl]-5-methoxy-3[(4-methyl-1-piperazinyl)methyl]-1H-indole of formula 6 in presence of ethanol and methanesulfonic acid at a temperature in the range of 15° C. to 35° C. for a period of 18 hours to 24 hours to obtain 1-[(2-bromophenyl)sulfonyl]-5-methoxy-3-[(4-methyl-1-piperazinyl)methyl]-1H-indole dimesylate of formula 7;

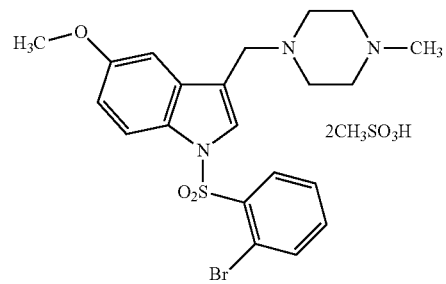
7

Step (vii): converting 1-[(2-bromophenyl)sulfonyl]-5-methoxy-3-[(4-methyl-1-piperazinyl)methyl]-1H-indole dimesylate of formula 7 in presence of aqueous ethanol and carbon slurry at a temperature in the range of 75° C. to 85° C. for a period of 0.5 hour-1.5 hours to obtain 1-[(2-bromophenyl)sulfonyl]-5-methoxy-3-[(4-methyl-1-piperazinyl)methyl]-1H-indole dimesylate monohydrate of formula (I).

2. The process as claimed in claim 1, wherein the temperature used in Step (i) is 20° C. to 30° C.

3. The process as claimed in claim 1, wherein the duration of reaction in Step (i) is 2 hours.

4. The process as claimed in claim 1, wherein the temperature used in Step (ii) is 20° C. to 35° C.

5. The process as claimed in claim 1, wherein the duration of reaction in Step (ii) is 3 hours.

6. The process as claimed in claim 1, wherein the temperature used in Step (v) is 25° C. to 35° C.

7. The process as claimed in claim 1, wherein the duration of reaction in Step (v) is 4 hours.

8. The process as claimed in claim 1, wherein the temperature used in Step (vi) is 25° C. to 30° C.

9. The process as claimed in claim 1, wherein the duration of reaction in Step (vi) is 24 hours.

10. The process as claimed in claim 1, wherein the temperature used in Step (vii) is 75° C. to 80° C.

11. The process as claimed in claim 1, wherein the duration of reaction in Step (vii) is 45 minutes.

12. The process as claimed in claim 1, wherein the purity of 1-[(2-bromophenyl)sulfonyl]-5-methoxy-3-[(4-methyl-1-piperazinyl)methyl]-1H-indole dimesylate monohydrate is greater than 99%.

* * * * *